US011896696B2

(12) United States Patent
Guthrie et al.

(10) Patent No.: US 11,896,696 B2
(45) Date of Patent: *Feb. 13, 2024

(54) METHODS OF SKIN WHITENING BY USE OF CANOLA EXTRACTS

(71) Applicant: 1242753 Ontario Inc., London (CA)

(72) Inventors: Najla Guthrie, Ontario (CA); Robert Allen Guthrie, Ontario (CA)

(73) Assignee: 1242753 Ontario Inc., London (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/842,686

(22) Filed: Apr. 7, 2020

(65) Prior Publication Data

US 2020/0397678 A1    Dec. 24, 2020

Related U.S. Application Data

(62) Division of application No. 16/242,266, filed on Jan. 8, 2019, now abandoned, which is a division of application No. 13/755,143, filed on Jan. 31, 2013, now Pat. No. 10,172,772.

(51) Int. Cl.
| A61K 8/368 | (2006.01) |
| A61K 8/365 | (2006.01) |
| A61Q 19/02 | (2006.01) |
| A61K 8/9789 | (2017.01) |

(52) U.S. Cl.
CPC .............. *A61K 8/368* (2013.01); *A61K 8/365* (2013.01); *A61K 8/9789* (2017.08); *A61Q 19/02* (2013.01)

(58) Field of Classification Search
CPC ...... A61K 8/368; A61K 8/9789; A61K 8/365; A61Q 19/02
See application file for complete search history.

(56) References Cited

U.S. PATENT DOCUMENTS

| 5,766,575 | A | 6/1998 | Crotty et al. |
| 9,125,887 | B2 | 9/2015 | Guthrie et al. |
| 10,172,772 | B2 * | 1/2019 | Guthrie .................. A61Q 19/02 |
| 2002/0090404 | A1 | 7/2002 | Guthrie et al. |
| 2002/0090405 | A1 | 7/2002 | Guthrie et al. |
| 2003/0072726 | A1 | 4/2003 | Banister et al. |
| 2007/0098824 | A1 | 5/2007 | Guthrie et al. |
| 2007/0166251 | A1 | 7/2007 | Dayan et al. |
| 2007/0274937 | A1 | 11/2007 | Dal Farra et al. |
| 2009/0317341 | A1 | 12/2009 | Madison |
| 2010/0143275 | A1 | 6/2010 | Guthrie et al. |
| 2010/0322886 | A1 | 12/2010 | Dal Farra et al. |
| 2014/0213652 | A1 | 7/2014 | Guthrie et al. |

FOREIGN PATENT DOCUMENTS

| EP | 1967175 | 9/2008 |
| FR | 2869228 | 10/2005 |
| JP | 2002536393 | 10/2002 |
| JP | 200616343 | 1/2006 |
| JP | 2009215266 | 9/2009 |
| JP | 2010520243 | 6/2010 |
| WO | WO-00/47179 | 8/2000 |
| WO | WO-02/22145 | 3/2002 |
| WO | WO-02/22146 | 3/2002 |
| WO | WO-2007/049137 | 5/2007 |
| WO | WO-2008/107093 | 9/2008 |
| WO | WO-2014/118610 | 8/2014 |

OTHER PUBLICATIONS

Latif et al. Enzyme-assisted aqueous extraction of oil and protein from canola (*Brassica napus*L.) seeds Eur. J. Lipid Sci. Technol. 2008,110,887-892. (Year: 2008).*
U.S. Appl. No. 11/260,758, dated Feb. 8, 2008 in the U.S. Patent and Trademark Office, Final Office Action.
U.S. Appl. No. 11/260,758, dated Mar. 12, 2007 in the U.S. Patent and Trademark Office, Requirement for Restriction/Election.
U.S. Appl. No. 11/260,758, dated Mar. 6, 2009 in the U.S. Patent and Trademark Office, Final Office Action.
U.S. Appl. No. 11/260,758, dated Jun. 16, 2008 in the U.S. Patent and Trademark Office, Office Action.
U.S. Appl. No. 11/260,758, dated Jul. 11, 2007 in the U.S. Patent and Trademark Office, Office Action.
U.S. Appl. No. 12/555,568, dated Jan. 30, 2015 in the U.S. Patent and Trademark Office, Notice of Allowance.
U.S. Appl. No. 12/555,568, dated Mar. 3, 2014 in the U.S. Patent and Trademark Office, Notice of Allowance.
U.S. Appl. No. 12/555,568, dated May 27, 2011 in the U.S. Patent and Trademark Office, Requirement for Restriction/Election.
U.S. Appl. No. 12/555,568, dated May 27, 2014 in the U.S. Patent and Trademark Office, Office Action.
U.S. Appl. No. 12/555,568, dated Jun. 1, 2015 in the U.S. Patent and Trademark Office, Notice of Allowance.
U.S. Appl. No. 12/555,568, dated Jul. 6, 2010 in the U.S. Patent and Trademark Office, Protest Documents filed by 3rd Party.
U.S. Appl. No. 13/755,143, dated Jan. 7, 2016 in the U.S. Patent and Trademark Office, Office Action.
U.S. Appl. No. 13/755,143, dated Oct. 3, 2014 in the U.S. Patent and Trademark Office, Final Office Action.
U.S. Appl. No. 13/755,143, dated Nov. 5, 2013 in the U.S. Patent and Trademark Office, Office Action.
U.S. Appl. No. 13/755,143, dated Nov. 8, 2017 in the U.S. Patent and Trademark Office, Office Action.
U.S. Appl. No. 13/755,143, dated Apr. 17, 2015 in the U.S. Patent and Trademark Office, Pre-Brief Appeal Conference decision.
U.S. Appl. No. 13/755,143, dated Jul. 14, 2016 in the U.S. Patent and Trademark Office, Final Office Action.

(Continued)

*Primary Examiner* — Jeffrey S Lundgren
*Assistant Examiner* — William Y Lee
(74) *Attorney, Agent, or Firm* — Arnall Golden Gregory LLP

(57) ABSTRACT

Compositions and methods for lightening skin are provided. A method for lightening skin may include the step of identifying skin where lightening or whitening is desired and topically applying to the skin a composition including (a) a skin lightening agent comprising a canola extract and (b) a cosmetically acceptable carrier. A method for treating hyperpigmentation may include the step of identifying skin containing areas of hyperpigmentation and topically applying to the skin a composition including (a) a canola extract and (b) a cosmetically acceptable carrier.

15 Claims, 6 Drawing Sheets

(56) References Cited

OTHER PUBLICATIONS

U.S. Appl. No. 13/755,143, dated Aug. 22, 2013 in the U.S. Patent and Trademark Office, Requirement for Restriction/Election.
U.S. Appl. No. 14/812,207, dated Dec. 21, 2017 in the U.S. Patent and Trademark Office, Notice of Allowance.
U.S. Appl. No. 16/242,266, dated Oct. 7, 2019 in the U.S. Patent and Trademark Office, Requirement for Restriction/Election.
"Anti-Melasma Whitening Essence," Database GNPD, URL: <http://www.gnpd.com>, Mintel, Jun. 2011.
Bhārata Bhaiṣajya Ratnākara—Compiled by Nagīnadāsa Chaganalāla Śāha, Translated by Gopinath Gupta—vol. IV: B. Jain Publishers, New Delhi, 2nd Ed., Reprint, Aug. 1999. [This book contains back references from 1000 B.C.to 20th century], p. 143. (abstract only).
Cakrapāṇidattah; Cakradattah—Translated by Indradeva Tripathi; Chaukhamba Sanskrit Samsthan (Varanasi), 4th Ed., 2002, p. 315. (abstract only).
Cao et al., "Acyl Coenzyme a Preference of Diacylglycerol Acyltransferase from the Maturing Seeds of *Cuphea*, Maize, Rapeseed, and Canola," Plant Physiol., 1987: 84, pp. 762-765.
Definition of Rapeseed, from Wikipedia, the free encyclopdeia, 2007.
DeVita et al., "Combination versus single agent chemotherapy: A review of the basis for selection of drug treatment of cancer," Cancer, 1975; 35, pp. 98-110.
Economic Research Service, USDA, "Crambe, Industrial Rapeseed, and Tung Provide Valuable Oils", Industrial Uses/ IUS-6/Sep. 1996, pp. 17-23.
European Supplementary Search Report in EP 14746867.2, dated Jul. 6, 2016.
Gadanigrahah ed, Ganga Sahaya Pandeya & Com.—Indradeva Tripathi, Part-3(Salakya-Pancakar ma Khanda) Chaukhamba Sanskrit Sansthan (Varanasi), 3rd Ed., 1999, p. 394. (abstract only).
Hawley's Condensed Chemical Dictionary, 13th Edition, 1997, p. 204.
Hu, "Methodology for evaluation of melanin content and production of pigment cells in Vitro," Photochem. Photobiol., 2008; 84(3): pp. 645-649.
International Search Report for relevant International Application No. PCT/IB2014/000019, dated Apr. 16, 2014, 4 pages.
International Search Report issued in related International Application No. PCT/IB2006/003020, dated Jun. 20, 2007.

Khattab et al., "Determination of sinapic acid derivatives in canola extracts using high-performance liquid chromatography," Journal of the American Oil Chemiste' Society, 87(2), 2010: pp. 147-155.
Kondra et al., "Inheritance of the Major Glucosinolates of Rapeseed (*Brassica napus*) Meal," Can. J. Plant Sci., 1970; 50(6): pp. 643-647.
Kozlowski et al., "Chapter 11: Phenotic Acids and Tannins in Rapeseed and Canola," In Chemistry, Analysis, and Nutritional Effects, published by Van Nostrand Reinhold; 1990, pp. 193-197, 201-202, 205, 207 and 209.
Mohammad Najmul Ghani Khan; Khazaain-al-Adiva, vol. II (20th century AD), Nadcem Yunus Printer / Sheikh Mohd Basheer & Sons, Lahore, 1911, p. 781. (abstract only).
Mohammad Najmul Ghani Khan; Qaraabaadeen Najm-al-Ghani (20th century AD), Munshi Nawal Kishorc, Lucknow, (Second Edition), 1928, p. 34. (abstract only).
Nydahl et al., "Similar Effects of Rapeseed Oil (Canola Oil) and Olive Oil in a Lipid-Lowering Diet for Patients with Hyperlipoproteinemia," Journal of the American College of Nutrition, 1995: 14(6), pp. 643-651.
Sodhala; Gadanigrahah ed,Ganga Sahaya Pandeya & Com.—Indradeva Tripathi, Part-3(Salakya-Pancakar ma Khanda) Chaukhamba Sanskrit Sansthan (Varanasi), 3rd Ed., 1999, pp. 394-395. (abstract only).
Stulberg, "Common hyperpigmentation disorders in adults: Part II. Melanoma, seborrheic keratoses, acenthosis nigricans, melasma, diabetic dermopathy, tinea versicolor," American Family Physician, 2003, [online], [retrieved on Dec. 17, 2015]. Retrieved from the Internet: <URL:http://66.197.58.78/ringworm_article_8.htm>.
Sun et al., "Acyl Coenzyme a Preference of the Glycerol Phosphate Pathway in the Microsomes from the Maturing Seeds of Palm, Maize, and Rapeseed," Plant Physiol., 1988: 88, pp. 56-60.
Vangasena—Commentator Shaligram Vaisya, Edited Shankar Ialji Jain; Khemraj Shrikrishna Das Prakashan; Bombay, Ed. 1996, p. 637. (abstract only).
Kozlowska et al., "Phenolic acids in oilseed flours," Nahrung, 1983; 27: pp. 449-453.
Wanasundara et al., "Isolation and Identification of an Antioxidative Component in Canola Meal," J. Agric. Food Chem., 1994; 42: pp. 1285-1290.
Kozlowska et al., "Phenolic Acids in Rapeseed and Mustard," JAOCS, 1983; 60(6): pp. 1119-1123.

* cited by examiner

METHODS OF SKIN WHITENING BY USE OF CANOLA EXTRACTS

CROSS-REFERENCE TO RELATED APPLICATIONS

This application is a divisional of U.S. application Ser. No. 16/242,266 filed Jan. 8, 2019, which is a divisional of U.S. application Ser. No. 13/755,143 filed Jan. 31, 2013, now granted as U.S. Pat. No. 10,172,772, the contents of which is incorporated by reference herein in its entirety.

FIELD OF THE INVENTION

The present invention relates generally to compositions of canola extracts containing high levels of phenolic acids and their methods of use to whiten skin.

BACKGROUND

In humans, melanin is the primary determinant of skin color. In the skin, specialized cells found in the basal layer of the dermis called melanocytes, produce melanin. Human possess similar concentrations of melanocytes in their skin, but present different concentrations of skin melanin based on their ethnicity.

Melanin plays an important biological role as a photoprotectant because it absorbs harmful UV radiation and transforms that energy into harmless heat. This property enables melanin to dissipate more than 99.9% of the absorbed UV radiation as heat. Melanogenesis, or increased production of melanin in human skin, is stimulated by UVB-radiation to produce what is commonly known as a tan. Although a tan appearance is desired by some people in various cultures, some cultures desire a lighter skin appearance. Further, melanin pigment disorders are perceived as cosmetic flaws. Examples of these local hyperpigmentations would be: freckles, melasma, chloasma, post-inflammatory hyperpigmentation, liver spots and many more. It is common to all forms of hyperpigmentation that a disturbance in the melanogenesis arises.

Various strategies have therefore been developed to reduce the pigmentation of the skin. One of the most often used skin and hair lighteners is hydroquinone or the hydroquinone glycoside of arbutin. However, these compounds have a cytotoxic effect on melanocytes and have an irritative effect on the skin. Another option is the inhibition of the synthesis of melanin by inhibiting the pacemaker enzyme tyrosinase. For this, the substances kojic acid and derivatives of kojic acid such as e.g. kojic acid dipalmitate kojic acid, azelaic acid, oxyresveratrol, linolenic acid, vitamin C and derivatives of ascorbic acid such as, for example, ascorbyl phosphate or ascorbyl palmitate, inter alia, are used. However, these substances have a high sensitizing potential, cause contact allergies, exhibit inadequate chemical stability in cosmetic formulations, or have only an unsatisfactory effect on the skin.

Moreover, strategies are also known which prevent the transfer of the melanin from the melanocytes into the surrounding keratinocytes. Thus, protease inhibitors are described which inhibit the PAR2 receptor on the surface of the keratinocytes and as a result reduce the transfer of the melanin. Hydrolysates from soya beans and niacinamide are said to reduce pigmentation in this way.

Increased renewal of the skin is also described for lightening the skin. For this procedure, alpha-hydroxy acids such as lactic acid and glycolic acid, inter alia, are used. By means of this treatment, the uppermost skin layers are corroded away and the melanin-containing corneocytes are abraded. A disadvantage of this method is frequent irritation of the skin.

There is thus an increasing need for new, further and improved compositions for decreasing melanin production in the skin and for treatment of hyperpigmentation. There is also a long-felt need for compositions which cosmetic lightening relatively large areas of pigmented skin.

The inventors are credited with creating a canola extract with high levels of phenolic acid that satisfies these long-felt commercial needs. It was an object of the invention to provide a care active ingredient which has a skin-lightening effect, which is well tolerated.

SUMMARY

The unmet need for compositions and methods to decrease melanin production in the skin and treat hyperpigmentation are solved by the compositions and methods of the illustrative embodiments described herein.

In one embodiment, a method for lightening skin is provided. This method includes the step of identifying skin where lightening or whitening is desired and topically applying to the skin a composition comprising: (a) a skin lightening agent comprising a canola extract and (b) a cosmetically acceptable carrier.

In another embodiment, a method for treatment of hyperpigmentation is provided. This method includes the step of identifying skin where hyperpigmentation is occurring and topically applying to the skin a composition comprising: (a) a canola extract and (b) a cosmetically acceptable carrier.

Other objects, features, and advantages of the illustrative embodiments will become apparent with reference to the drawings and detailed description that follow.

DETAILED DESCRIPTION OF ILLUSTRATIVE EMBODIMENTS

Figure 1:
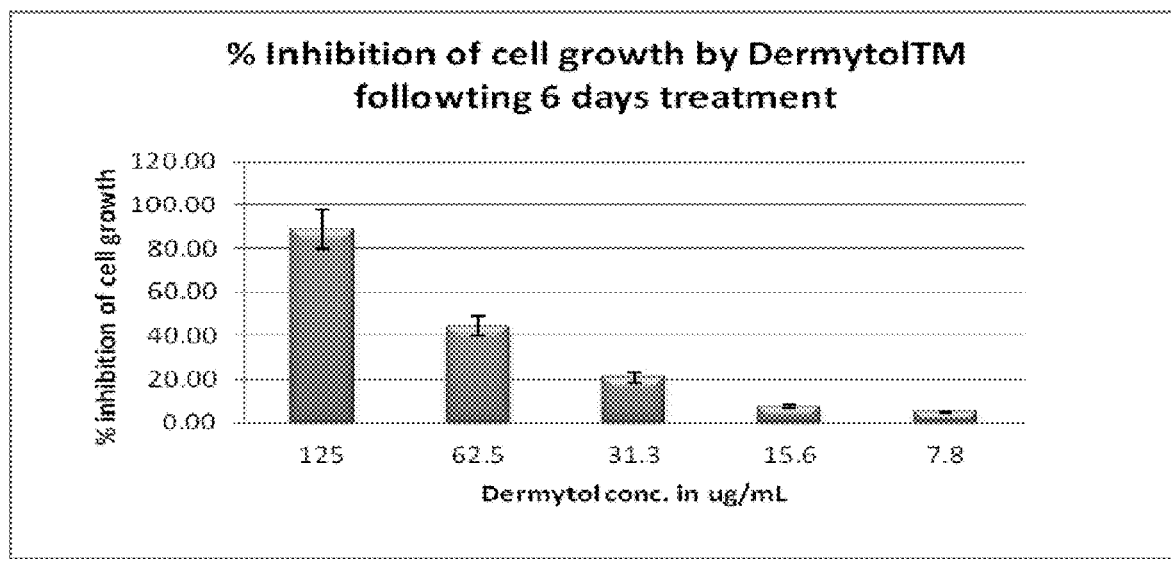
FIG. 1 is a bar chart illustrating the effects of a high phenolic acid canola extract on growth inhibition of NHEM Cells after 6 days of culture.

In the following detailed description of the illustrative embodiments, it is understood that these embodiments are described in sufficient detail to enable those skilled in the art to practice the invention, and it is understood that other embodiments may be utilized and that logical structural and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

This invention provides for a method for lightening skin. This method includes the step of identifying skin where lightening or whitening is desired and topically applying to the skin a composition comprising a skin lightening agent, where the agent comprises a canola extract containing high levels of phenolic acids such as sinapic acid.

In another embodiment, a method for treatment of hyperpigmentation is provided. This method includes the step of identifying skin where hyperpigmentation is occurring and topically applying to the skin a composition comprising: (a) one or more of protocatechuic acid, vanilic acid, caffeic acid, syringic acid, P-coumaric acid, and sinapic acid and (b) a cosmetically acceptable carrier.

High Phenolic Acid Canola Compositions

In preferred embodiments, the canola extract comprises one or more of protocatechuic acid, vanilic acid, caffeic acid, syringic acid, P-coumaric acid, and sinapic acid.

In other preferred embodiments, the canola extract is selected from the group consisting of a total phenolic, a phenolic acid, a carotenoid, a tocopherol/sterol, a glucosinolate, and combinations thereof. In certain embodiments, the combination is a glucosinolate and a phenolic.

The canola extract may be incorporated into the formulation in an amount to provide a concentration effective to lighten skin. The concentration can be, e.g. from about 0.01 µg/ml to about 10000µ/ml. This range is not meant to be limiting as one skilled in the art would be able to determine the effective concentration range to provide the desired effect. The invention is intended to cover any concentration of at least one canola extract which exhibits a lightening effect on skin.

In certain embodiments, the composition of canola extract comprises a dose of tocopherol/sterol to provide, e.g., a concentration of the tocopherol/sterol from about 0.1 µg/ml to about 500 µg/ml, about 25 µg/ml to about 250 µg/ml or from about 100 µg/ml to about 200 µg/ml.

In certain embodiments, the composition of canola extract comprises a dose of phenolic acids to provide, e.g., a concentration from about 0.1 µg/ml to about 1000 µg/ml, from about 125 µg/ml to about 600 µg/ml, from about 250 µg/ml to about 600 µg/ml or from about 400 µg/ml to about 600 µg/ml.

In certain embodiments, the composition of canola extract comprises a dose of glucosinolate/phenolics to provide, e.g., a concentration from about 0.1 µg/ml to about 1000 µg/ml, from about 10 µg/ml to about 600 µg/ml, from about 150 µg/ml to about 600 µg/ml; or from about 300 µg/ml to about 600 µg/ml.

In certain embodiments, the composition of canola extract comprises a dose of sinapic acid to provide a concentration, e.g., from about µg/ml to about 500 µg/ml; from about 10 µg/ml to about 400 µg/ml; or from about 40 µg/ml to about 200 µg/ml.

In embodiments where the canola extract comprises a glucosinolate, the glucosinolate can be selected from the group consisting of progoitrin, sinigrin, glucoraphanin, napoleferin, glucoalyssin, gluconapin, 4-hydroxybrassicin, glucobrassicanapin, glucobrassicin, gluconasturtin, 4-methoxy-glucobrassicin, neoglucobrassicin and combinations thereof.

In certain embodiments, the present invention is directed to a canola extract comprising at least 30% sinapic acid, preferably at least 40% sinapic acid, and most preferably at least 50% sinapic acid.

In certain embodiments, the present invention is directed to a canola extract comprising from about 40% to about 60% sinapic acid; or about 45% to about 55% sinapic acid.

In certain embodiments, the present invention is directed to a topical pharmaceutical formulation comprising a canola extract comprising greater than 30% sinapic acid, greater than 40% sinapic acid, or greater than 50% sinapic acid; and a pharmaceutically acceptable carrier suitable for topical administration.

In certain embodiments, the present invention is directed to a topical pharmaceutical formulation comprising a canola extract comprising from about 40% to about 60% sinapic acid, or from about 45% to about 55% sinapic acid; and a pharmaceutically acceptable carrier suitable for topical administration.

In certain embodiments, the present invention is directed to a topical pharmaceutical formulation comprising an amount of canola extract to provide from about 0.1% to about 5%, from about 0.2% to about 2.5% sinapic acid, or from about 0.4% to about 0.8% sinapic acid; and a pharmaceutically acceptable carrier suitable for topical administration.

In certain embodiments, the present invention is directed to a topical pharmaceutical formulation comprising from about 0.1% to about 5% sinapic acid, from about 0.2% to about 2.5% sinapic acid, or from about 0.4% to about 0.8% sinapic acid; and a pharmaceutically acceptable carrier suitable for topical administration.

In certain embodiments, the topical pharmaceutical formulation of the present invention is selected from the solution, a suspension, an emulsion, a lotion, an ointment, a gel, a cream, or an oil.

In certain embodiments, the invention is directed to a transdermal delivery system comprising a transdermal delivery device and a topical pharmaceutical formulation as disclosed herein. In certain embodiments, the transdermal delivery device is selected from the group consisting of a transdermal patch, a transdermal plaster, a transdermal disc and an iontophoretic transdermal device.

In certain embodiments, the present invention is directed to a topical sunscreen formulation comprising a sunblocking agent, a canola extract, and a pharmaceutically acceptable carrier suitable for topical administration.

In the topical sunscreen formulations of the present invention, the sunblocking agent can be selected from the group consisting of oxybenzone, sulisobenzone, dioxybenzone, menthyl anthranilate, para aminobenzoic acid (PABA), octyl methoxycinnamate, octocrylene, drometrizole trisiloxane, octyl salicylate, homomenthyl salicylate, octyl dimethyl PABA, TEA salicylate, butylmethoxy dibenzoylmethane (avobenzone), 4-methyl benzylidene camphor, 3-benzylidene camphor, benzylidene camphor sulfonic acid, octyl triazone, terephthalydiene dicamphor sulfonic acid, ethyl PABA, hydroxy methylphenyl benzotriazole, methylene bis-benzotriazoyltetramethylbutylphenol, diethylhexyl-2,6-naphthalate, di-t-butyl hydroxybenzylidene camphor, bis-ethylhexyloxyphenol methoxyphenol triazine, titanium dioxide, zinc oxide, and any combinations thereof.

The exact amount of sunscreen employed in the compositions can vary depending upon the degree of protection desired from the sun's UV radiation. In certain embodiments, the sunblocking agent is present at up to about 70 wt %, at about 0.05 wt % to about 50 wt %, or at about 0.5 wt % to about 30 wt %, based on the total weight of the formulation.

In certain embodiments, the sunscreen formulation exhibits an SPF of about 2 to about 70, or from about 15 to about 45.

In certain embodiments, the present invention is directed to an oral pharmaceutical formulation comprising a canola extract comprising at least 30% sinapic acid, preferably at least 40% sinapic acid, and most preferably at least 50% sinapic acid; and a pharmaceutically acceptable excipient.

In certain embodiments, the present invention is directed to an oral pharmaceutical formulation comprising a canola extract comprising from about 40% to about 60% sinapic acid, or from about 45% to about 55% sinapic acid; and a pharmaceutically acceptable excipient.

In certain embodiments, the oral pharmaceutical formulation is in the form a liquid, a tablet, a capsule, a gelcap, or a powder.

The canola extract of the present invention can be incorporated into the formulations of the present invention in an amount to provide the desired pharmacodynamic action (i.e., an anti-proliferative effect, or antihyperlipidemic effect). The concentration can be, e.g. from about 0.01 to about 10000 µg/ml. This range is not meant to be limiting as one skilled in the art would be able to determine the effective concentration range to provide the desired effect.

In certain embodiments, the composition of canola extract comprises a dose of phenolic acids to provide, e.g., a concentration from about 0.1 to about 1000 µg/ml, from about 125 to about 600 µg/ml, from about 250 to about 600 µg/ml or from about 400 to about 600 µg/ml.

In certain embodiments, the composition of canola extract comprises a dose of sinapic acid to provide a concentration, e.g., from about 1 to about 500 µg/ml; from about 10 to about 400 µg/ml; or from about 40 to about 200 µg/ml.

In certain embodiments, the pharmaceutical compositions of the present invention reduce elevated lipoproteins by about 25% or more, by about 50% or more or about 75% or more, depending on the individual needs of the patient.

In certain embodiments the canola extract of the present invention may also be administered with another compound capable of lowering blood levels of triglycerides, cholesterol, or glycerol, including but not limited to fibrates (e.g., bezafibrate, gemfibrozil, and clofibrate), HMG-COA reductase inhibitors (e.g., somatostatin, pravastatin, simvastatin, and fluorastatin, atorvastatin, and lovastatin), bile acid binding resins (e.g., cholestyramine and colestipol), nicotinic acid compounds (e.g., nicotinic acid and niceritrol), and fish oils. The additional compound can be administered before, with or after the canola extract.

The present invention can be administered intravenously, intraperitoneally, subcutaneously, intramuscularly, intrathecally, orally, sublingually, into the buccal cavity, rectally, topically or by aerosol.

Formulations suitable for oral administration include liquid solutions of the active compound dissolved in diluents such as saline, water or PEG 400; capsules or tablets, each containing a predetermined amount of the active agent as solid, granules or gelatin; suspensions in an approximate medium; and emulsions.

Formulations suitable for parenteral administration include aqueous and non-aqueous isotonic sterile solutions, which contain buffers, antioxidants and preservatives. The formulations may be in unit dose or multi-dose sealed containers.

In certain embodiments, the compounds of the present invention can be administered in a local manner, for example, via injection of the compound directly into a desired location, often in a depot or sustained release formulation.

In cases of local administration or selective uptake, the effective local concentration of the drug may not be related to plasma concentration.

In certain embodiments, the present invention is directed to a method for extracting phenolic acids from canola meal comprising (a) homogenizing the canola meal; and (b) drying the homogenized mixture (e.g., by evaporation or freeze drying).

In certain embodiments, the canola meal is homogenized in menthol:water, preferably in a ratio of 5:5 to 9:1, preferably the ratio is about 7:3.

In certain embodiments, the present invention is directed to a method for extracting phenolic acids from canola meal comprising (a) mixing canola meal containing phenolic acid esters in a solvent; (b) hydrolyzing the phenolic acid esters with a base; (c) acidifying the mixture; and (d) freeze drying the mixture to obtain an extraction.

In certain embodiments, the present invention is directed to a method for extracting phenolic acids from canola meal comprising (a) mixing canola meal containing phenolic acid esters in a solvent; (b) hydrolyzing the phenolic acid esters with a base; (c) acidifying the mixture; and (d) extracting phenolic acid with a second solvent consisting essentially of ethyl acetate.

In certain embodiments, the solvent comprises methanol:water in a ratio of 5:5 to 9:1, preferably the ratio is about 7:3.

In certain embodiments, the base can be an organic or inorganic base or alkaline agent such as sodium carbonate, sodium bicarbonate, sodium phosphate dibasic, sodium phosphate tribasic, sodium citrate, magnesium hydroxide, magnesium carbonate, calcium carbonate, calcium phosphate, sodium hydroxide, tribasic phosphate, potassium phosphate and mixtures thereof A preferred base is sodium hydroxide.

In certain embodiments, the present invention further comprises extracting phenolic acid with an alkyl acetate (preferably ethyl acetate) after acidification and resuspending the extraction is a second solvent prior to freeze drying. Preferably, the second solvent is methanol.

In certain embodiments, the present invention further comprises washing the freeze dried extraction with a third solvent. Preferably, the third solvent is hexane. In further embodiments, the extraction is filtered and dried, e.g., by evaporation.

In certain embodiments, the acidifying step is to a pH of less than 5, preferably to a pH of about 2. The acidifying step can be performed with any suitable organic or inorganic acidic material, e.g., inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like.

For this, the substances kojic acid and derivatives of kojic acid such as e.g. kojic acid dipalmitate kojic acid, azelaic acid, oxyresveratrol, linolenic acid, vitamin C and derivatives of ascorbic acid such as, for example, ascorbyl phosphate or ascorbyl palmitate, inter alia, are used. However, these substances either have a high sensitizing potential, cause contact allergies, exhibit inadequate chemical stability in cosmetic formulations or have only an unsatisfactory effect on the skin.

The composition of the present invention may use commercially acceptable and conventional vehicles may be used, acting as diluents, dispersants and/or carriers for the skin lightening agents and additives described herein and for any other optional but often preferred ingredients. Therefore, the cosmetically acceptable vehicle suitable for use in this invention may be aqueous-based, anhydrous or an emulsion whereby a water-in-oil or oil-in-water emulsion is generally preferred. If the use of water is desired, water typically makes up the balance of the cosmetic composition, and preferably, makes up from about 5 to about 99%, and most preferably, from about 40 to about 80% by weight of the cosmetic composition, including all ranges subsumed therein.

In addition to water, organic solvents may be optionally included to act as carriers or to assist carriers within the cosmetic compositions of the present invention. Illustrative and non-limiting examples of the types of organic solvents suitable for use in the present invention include alkanols like ethyl and isopropyl alcohol, mixtures thereof or the like.

Other optional additives suitable for use include ester oils such as isopropyl myristate, cetyl myristate, 2-octyldodecyl myristate, avocado oil, almond oil, olive oil, neopentylglycol dicaprate, mixtures thereof or the like.

Emollients may also be used as a carriers within the cosmetic composition of the present invention. Alcohols like 1-hexadecanol (i.e., cetyl alcohol) are often desired as are the emollients generally classified as silicone oils and synthetic esters. Silicone oils suitable for use include cyclic or linear polydimethylsiloxanes containing from 3 to 9 silicon atoms. Nonvolatile silicone oils useful as an emollient material in the inventive cosmetic composition described herein include polyalkyl siloxanes, polyalkylaryl siloxanes and polyether siloxane copolymers.

The ester emollients that may optionally be used are: (1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate. (2) Ether-esters such as fatty acid esters of ethoxylated fatty alcohols. (3) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. (4) Wax esters such as beeswax, spermaceti, stearyl stearate and arachidyl behenate. (5) Sterols esters, of which cholesterol fatty acid esters are examples.

Emollients when used, may comprise about 0.1 to about 50% by weight of the cosmetic composition, including all ranges subsumed therein.

Fatty acids may also be included as cosmetically acceptable carriers within the composition of the present invention. Illustrative examples of such fatty acids include pelargonic, lauric, myristic, palmitic, stearic, isostearic, oleic, linoleic, arachidic, behenic or erucic acid, and mixtures thereof. Compounds that enhance skin penetration, like dimethyl sulfoxide, may also be used.

Humectants of the polyhydric alcohol type may also be employed in the cosmetic compositions of this invention. The humectant often aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from about 0.2 to about 25%, and preferably, from about 0.5 to about 15% by weight of the cosmetic composition, based on total weight of the cosmetic composition and including all ranges subsumed therein.

Thickeners may also be utilized as part of the cosmetically acceptable carrier in the cosmetic compositions of the present invention. Typical thickeners include cross-linked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, *sclerotium*, carrageenan, pectin and combinations of these gums. Amounts of the thickener may range from 0.0 to 5%, usually from 0.001 to 1%, optimally from 0.01 to 0.5% by weight.

Collectively, the water, solvents, silicones, esters, fatty acids, humectants and/or thickeners will constitute the cosmetically acceptable carrier in amounts from 1 to 99.9%, preferably from 80 to 99% by weight.

Surfactants may also be present in cosmetic compositions of the present invention. Total concentration of the surfactant will range from about 0 to about 40%, and preferably, from about 0 to about 20%, optimally from about 0 to about 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; mono- and di-fatty acid esters of ethylene glycol; fatty acid monoglyceride; sorbitan, mono- and di-$C_8$-$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, acyl glutamates, $C_8$-$C_{20}$ alkyl ether phosphates and combinations thereof.

Perfumes may be used in the cosmetic composition of this invention. Illustrative yet non-limiting examples of the types of fragrances that may be used in this invention include myrcene, dihydromyrenol, citral, tagetone, cis-geranic acid, citronellic acid, mixtures thereof or the like. Preferably, the amount of fragrance employed in the cosmetic composition of this invention is in the range from about 0.0% to about 10%, more preferably, about 0.00001% to about 5 wt %, most preferably, about 0.0001% to about 2%.

Various types of optional additional active ingredients may be used in the cosmetic compositions of the present invention. Actives are defined as skin benefit agents other than emollients and other than ingredients that merely improve the physical characteristics of the composition. Although not limited to this category, general examples include talcs and silicas, as well as alpha-hydroxy acids, beta-hydroxy acids and zinc salts.

Beta-hydroxy acids include salicylic acid, for example. Zinc pyrithione is an example of the zinc salts useful in the cosmetic composition of the present invention.

Many cosmetic compositions, especially those containing water, should be protected against the growth of potentially harmful microorganisms. Anti-microbial compounds, such as triclosan, and preservatives are, therefore, typically necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the cosmetic composition.

Still other optional ingredients that may be used with the cosmetic composition of this invention include dioic acids (e.g., malonic acid, sebacic acid), antioxidants like vitamin E, retinoids, including retinoic acid, retinal, retinol and retinyl esters, conjugated linoleic acid, petroselinic acid and mixtures thereof, as well as any other conventional ingredients well known for wrinkle-reducing, anti-acne effects and reducing the impact of sebum.

Even other optional ingredients that may be employed in the cosmetic composition of the present invention are skin lightening sources in addition to the skin lightening additive described in this invention. Illustrative yet non-limiting examples of skin lightening sources that may be used along with the skin lightening additives of this invention are niacinamide, vitamin C and its derivatives, 12-hydroxystearic acid, resorcinols and their derivatives (including those esterified with, for example, ferulic acid, vanillic acid or the like), extracts of kudzu, chamomile, and yarrow as well as any mixtures of the skin lightening sources in addition to skin lightening additive.

The cosmetic compositions of the present invention are intended for use primarily as a product for topical application to human skin, especially and at least as a product for lightening the skin. Thus, the inventor has discovered that the described additives unexpectedly have skin lightening capabilities whereby the same may be employed as skin lightening additives in topical cosmetic compositions that are applied to areas of the skin where lightening or whitening is desired. Other benefits from using the cosmetic composition of this invention may include skin moisturizing, decreasing the effect of sebum on the skin and skin wrinkle reducing. Often, the cosmetic composition of the present invention has a melting point from about 30.degree. C. to about 45.degree. C., including all ranges subsumed therein. In an especially preferred embodiment, the cosmetic composition of the present invention has a pH from about 4.5 to about 7.5, including all ranges subsumed therein.

It should be apparent from the foregoing that an invention having significant advantages has been provided. While the invention is shown in only a few of its forms, it is not just limited but is susceptible to various changes and modifications without departing from the spirit thereof.

Example 1

Cell Culture

NHEM (skin, normal melanocyte) cell line obtained from PROMOCELL were cultured according to the supplier's instructions. Briefly, cells were maintained in M2 (melanocyte complete growth medium, PROMOCELL) supplemented with 10% FBS in a humidified chamber at 37° C., 5% $CO_2$. Cells were plated in 12 well tissue culture plates (3 well per concentration) at $1\times10^5$ cells/well (1 ml of $1\times10^5$ cells/ml) and incubated overnight to allow cells to adhere to the plate surface. An initial reading of melanin concentration was measured at 475 nm wavelength with spectrophotometer.

Treatment of Cells and Harvesting of Wells and Melanin Assay

The high phenolic acid canola extract, which the inventors also call Dermytol™, compound was weighed and prepared immediately before use by dissolving in distilled water at a concentration of 10 mg/mL Dermytol™ is formed of:

| Compound | Pro A | Van A | Caf A | Syr A | Pco A | Sin A | Total |
|---|---|---|---|---|---|---|---|
| % (w/w) | 0.019233 | 0.009704 | 0.0439 | 0.014985 | 0.044455 | 0.236625 | 0.368902 |

A dilution of 2 mg/mL of Dermytol™ was prepared using complete media prepared for NHEM cells and sterile filtered using a 0.2 µm syringe filter. Serial dilutions were prepared with media and cells treated at the following concentrations 125 µg/mL, 62.5 µg/mL, 31.3 µg/mL, 15.6 µg/mL and 7.8 µg/mL. Media controls received only complete media.

After the overnight incubation, cells were treated with media control and a article. Each concentration was plated in triplicate wells. The wells were incubated for 6 days in a humidified chamber at 37° C., 5% $CO_2$ after which time the wells were washed with PBS and trypsinized and live cells counted with trypan blue in a hemocytometer. Cell suspensions were centrifuged and pellet dissolved in 1N NaOH. Melanin concentration was determined by measurement of optic density at 475 nm.

A melanin standard curve was prepared by dissolving melanin (sigma) at various dilutions in NaOH (1N) and measuring the absorbance at 475 nm with a validated spectrophotometer.

Resulting data was prepared graphically for MPT, melanin production in a culture well (area) per day by comparing with media controls.

Results

As illustrated in below Table 1, increasing concentrations of Dermytol™ resulted in increased inhibition of NHEM cell growth.

TABLE 1

| Treatment Conc. ug/mL | % Inhibition of NHEM cell growth with Dermytol ™ |
| --- | --- |
| 125 | 88.89 |
| 62.5 | 44.44 |
| 31.3 | 20.89 |
| 15.6 | 7.56 |
| 7.8 | 4.89 |

FIG. 1 further represents the effect of Dermytol™ on growth inhibition of NHEM Cells after 6 days of culture. This graph shows that at higher concentration (125 ug/mL) there was 88.89% inhibition of NHEM cell growth. However concentration from 62.5 ug/mL to 7.8 ug/mL a dose dependent inhibition is visible.

Table 2 shown below represents the data of Melanin Production per Treatment per culture area per day (MPT).

TABLE 2

| Treatment Conc. ug/mL | Well No. | Melanin Conc. (mg/mL) | Avg. Melanin Conc. (mg/mL) | STDEV | CV % | MPT in µg per well per day |
| --- | --- | --- | --- | --- | --- | --- |
| Control | 1 | 0.165 | 0.168 | 0.003 | 1.58 | 20.08 |
| | 2 | 0.170 | | | | |
| | 3 | 0.170 | | | | |
| 125 | 1 | 0.066 | 0.072 | 0.005 | 6.97 | 3.99 |
| | 2 | 0.074 | | | | |
| | 3 | 0.075 | | | | |
| 62.5 | 1 | 0.091 | 0.087 | 0.005 | 5.77 | 6.47 |
| | 2 | 0.081 | | | | |
| | 3 | 0.088 | | | | |
| 31.3 | 1 | 0.113 | 0.104 | 0.010 | 9.26 | 9.41 |
| | 2 | 0.094 | | | | |
| | 3 | 0.106 | | | | |
| 15.6 | 1 | 0.133 | 0.128 | 0.004 | 3.09 | 13.37 |
| | 2 | 0.127 | | | | |
| | 3 | 0.125 | | | | |
| 7.8 | 1 | 0.148 | 0.149 | 0.003 | 2.00 | 16.78 |
| | 2 | 0.152 | | | | |
| | 3 | 0.146 | | | | |

Figure 2:
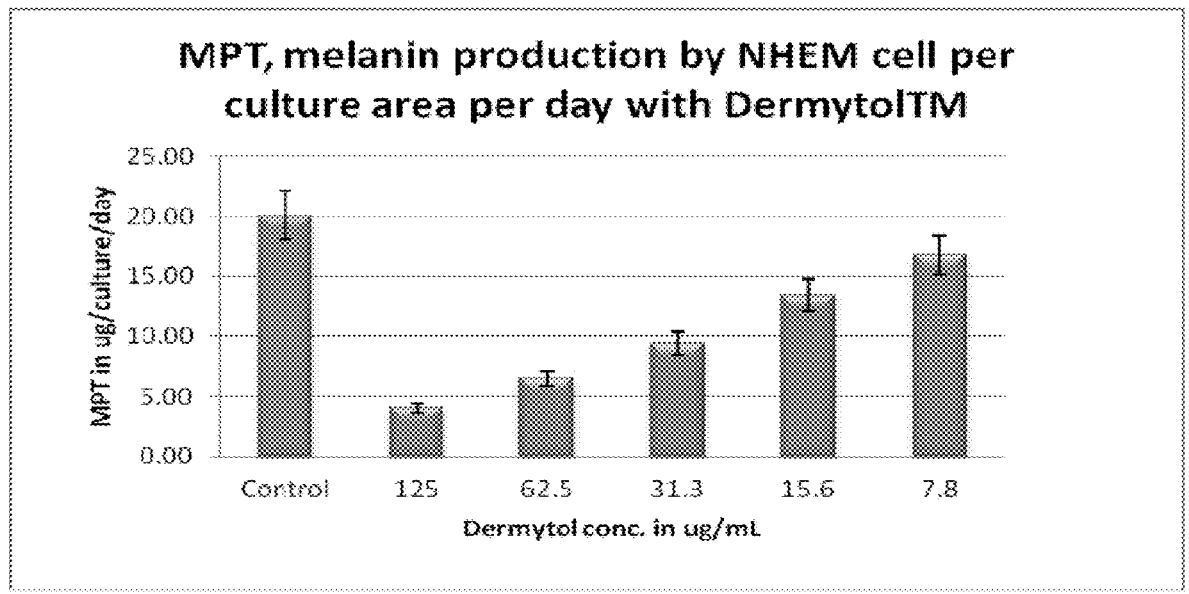
FIG. 2 is a bar chart illustrating the effects of a high phenolic acid canola extract on production of melanin by NHEM cells after 6 days of culture.

FIG. 2 further represents the effect of Dermytol™ on production of melanin by NHEM cells after 6 days of culture (MPT).

Biological and cosmetic effects of melanin in vivo are determined by melanin content per area, not per cell. For this reason melanin content per area (culture) is a better parameter than melanin content per cell, for the evaluation of changes in melanin content after treatment in vitro (Dan-Ning, et al. Methodology for evaluation of melanin content and production of pigment cells in vitro. *Photochem. Photobiol.* 2008 May-June; 84(3):645-9). FIG. 2 shows that production of melanin per culture well per day was inversely proportionate to Dermytol™ treatment doses compared to media control.

Table 3 below represents percent inhibition of melanin production with Dermytol™ per well per day.

TABLE 3

| Treatment Conc. ug/mL | % Inhibition of Melanin Production per culture per day |
| --- | --- |
| 125 | 80.11 |
| 62.5 | 67.80 |
| 31.3 | 53.16 |
| 15.6 | 33.44 |
| 7.8 | 16.45 |

Figure 3:
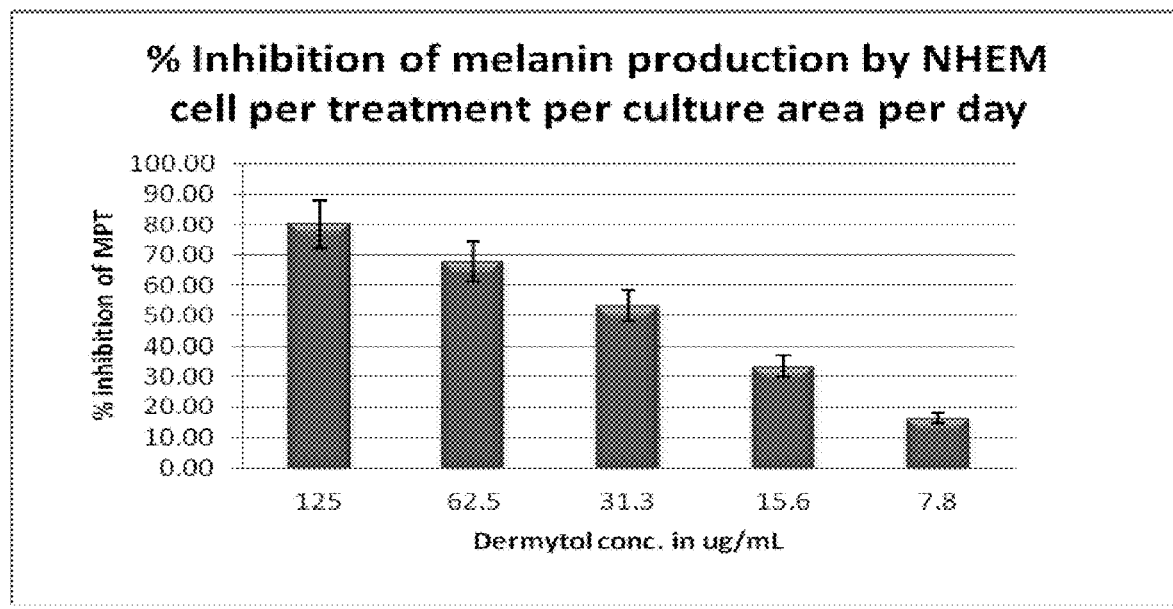
FIG. 3 is a bar chart illustrating the effects of a high phenolic acid canola extract on inhibition of melanin production by NHEM cells after 6 days of treatment.

FIG. 3 further represents effect of Dermytol™ on inhibition of melanin production by NHEM cells after 6 days of treatment. This graph shows that at concentration 125 ug/mL the melanin production by A375 cells was decreased by 80.11% compared to the controls. A dose dependent inhibition response can also be seen in FIG. 3.

Taken together, these results illustrate that melanin production is decreased in cells after treatment with Dermytol™ at concentration 15.6 ug/mL. At concentration 15.6 ug/mL, cell viability was reduced 7.56% while melanin production was inhibited by 33.44%. At higher concentrations, 31.3 ug/mL and 62.5 ug/mL cell viability was reduced by 20.89% and 44.44% respectively. Melanin inhibition was 53.16% at concentration 31.3 ug/mL and 67.80% at concentration 62.5 ug/mL.

Example 2

Cell Culture

A375 (skin, malignant melanoma) cell line obtained from ATCC were cultured according to the supplier's instructions. Briefly, cells were maintained in DMEM supplemented with 10% FBS in a humidified chamber at 37° C., 5% $CO_2$. Cells were plated in 27 $T_{25}$ tissue culture flasks (3 flask per concentration) at $1\times10^6$ cells/flask (1 ml of $1\times10^6$ cells/ml) and incubated overnight to allow cells to adhere to the plate surface. An initial reading of melanin concentration was measured at 475 nm wavelength with spectrophotometer.

Treatment of Cells and Harvesting of Flasks and Melanin Assay

The high phenolic acid canola extract, which the inventors also call Dermytol™, compound was weighed and prepared immediately before use by dissolving in distilled water at a concentration of 10 mg/mL. Dermytol™ is formed of:

| Compound | Pro A | Van A | Caf A | Syr A | Pco A | Sin A | Total |
| --- | --- | --- | --- | --- | --- | --- | --- |
| % (w/w) | 0.019233 | 0.009704 | 0.0439 | 0.014985 | 0.044455 | 0.236625 | 0.368902 |

A dilution of 2 mg/mL was prepared using complete media prepared for A375 cells and sterile filtered using a 0.2 µm syringe filter and syringe. Serial dilutions were prepared with media and cells treated at the following concentrations 1000 µg/mL, 500 µg/mL, 250 µg/mL, 125 µg/mL, 62.5 µg/mL, 31.3 µg/mL, 15.6 µg/mL and 7.8 µg/mL Media controls received only complete media.

After the overnight incubation, cells were treated with media control and the test article. Each concentration was plated in triplicate flasks. The flasks were incubated for 6 days in a humidified chamber at 37° C., 5% $CO_2$ after which time the flasks were washed with PBS and trypsinized and live cells counted with trypan blue in a hemocytometer. Cell suspensions were centrifuged and pellet dissolved in 1N NaOH. Melanin concentration was determined by measurement of optic density at 475 nm.

A melanin standard curve was prepared by dissolving melanin (sigma) at various dilutions in NaOH (1N) and measuring the absorbance at 475 nm with a validated spectrophotometer.

Resulting data was prepared graphically for MPT, melanin production in a culture flask (area) per day by comparing with media controls.

Results

Table 4 below represents live cell count per treatment per flask

TABLE 4

| Dermytol ™ Treatment Conc. ug/mL | Live Cell Count with trypan blue/flask |
| --- | --- |
| Control | 1090000 |
| 1000 | 0 |
| 500 | 0 |
| 250 | 0 |
| 125 | 0 |
| 62.5 | 680000 |
| 31.3 | 790000 |
| 15.6 | 960000 |
| 7.8 | 999000 |

Figure 4:
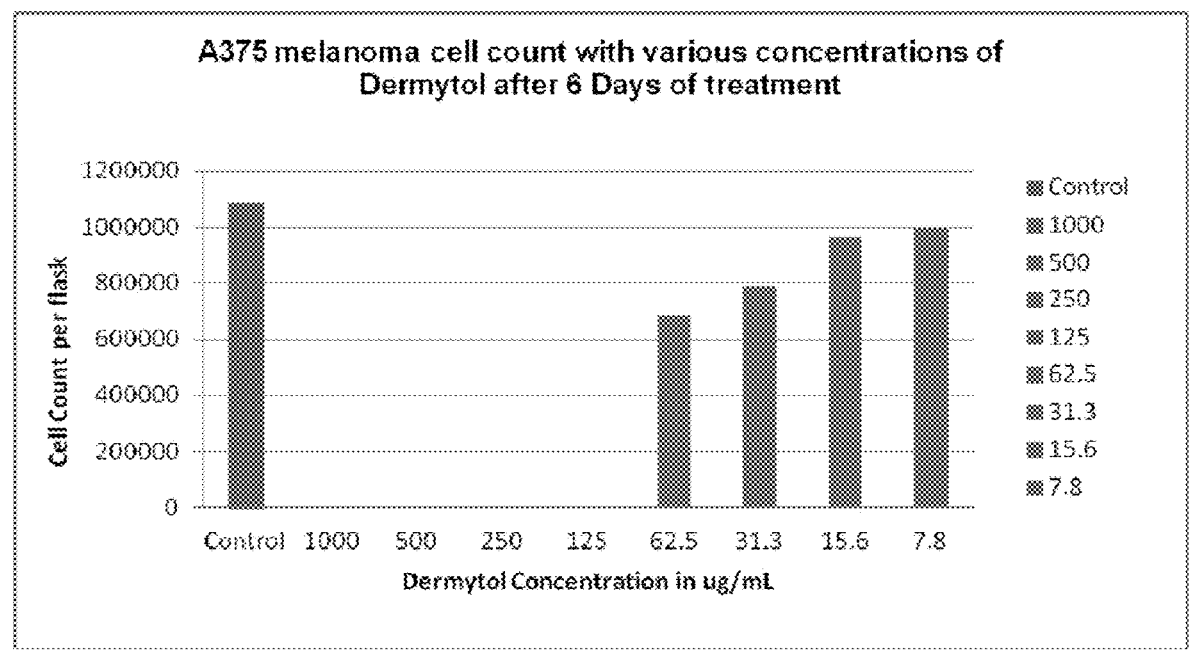
FIG. 4 is a bar chart illustrating the effects of a high phenolic acid canola extract on growth of A375 Cells after 6 days of culture.

Effects of Dermytol™ on growth of A375 Cells After 6 days of culture is illustrated in FIG. 4. FIG. 4 shows that at higher concentration of Dermytol™ (1000 ug/mL to 125 ug/mL) all A375 cells were dead. However concentration from 62.5 ug/mL to 7.8 ug/mL a dose dependent viability is visible.

Table 5 below represents Melanin Production per Treatment per culture area per day (MPT).

TABLE 5

| Treatment Conc. ug/mL | Flask Number | Melanin Conc. (mg/mL) | Ave. Melanin Conc. (mg/mL) | STDEV | CV % | MPT in µg per flask per day |
| --- | --- | --- | --- | --- | --- | --- |
| Control | 1 | 0.708 | 0.726 | 0.016 | 2.196 | 68.714 |
| | 2 | 0.732 | | | | |
| | 3 | 0.739 | | | | |
| 1000 | 1 | 0.728 | 0.722 | 0.014 | 1.893 | 0.000 |
| | 2 | 0.707 | | | | |
| | 3 | 0.733 | | | | |
| 500 | 1 | 0.633 | 0.630 | 0.006 | 0.925 | 0.000 |
| | 2 | 0.623 | | | | |
| | 3 | 0.633 | | | | |
| 250 | 1 | 0.527 | 0.531 | 0.004 | 0.791 | 0.000 |
| | 2 | 0.535 | | | | |
| | 3 | 0.532 | | | | |
| 125 | 1 | 0.495 | 0.481 | 0.013 | 2.743 | 0.000 |
| | 2 | 0.469 | | | | |
| | 3 | 0.480 | | | | |
| 62.5 | 1 | 0.598 | 0.571 | 0.026 | 4.551 | 42.915 |
| | 2 | 0.547 | | | | |
| | 3 | 0.570 | | | | |
| 31.3 | 1 | 0.622 | 0.616 | 0.019 | 3.040 | 50.296 |
| | 2 | 0.595 | | | | |
| | 3 | 0.631 | | | | |
| 15.6 | 1 | 0.602 | 0.627 | 0.034 | 5.460 | 52.178 |
| | 2 | 0.613 | | | | |
| | 3 | 0.666 | | | | |

TABLE 5-continued

| Treatment Conc. ug/mL | Flask Number | Melanin Conc. (mg/mL) | Ave. Melanin Conc. (mg/mL) | STDEV | CV % | MPT in µg per flask per day |
| --- | --- | --- | --- | --- | --- | --- |
| 7.8 | 1 | 0.705 | 0.717 | 0.012 | 1.606 | 67.173 |
| | 2 | 0.727 | | | | |
| | 3 | 0.719 | | | | |

Figure 5:
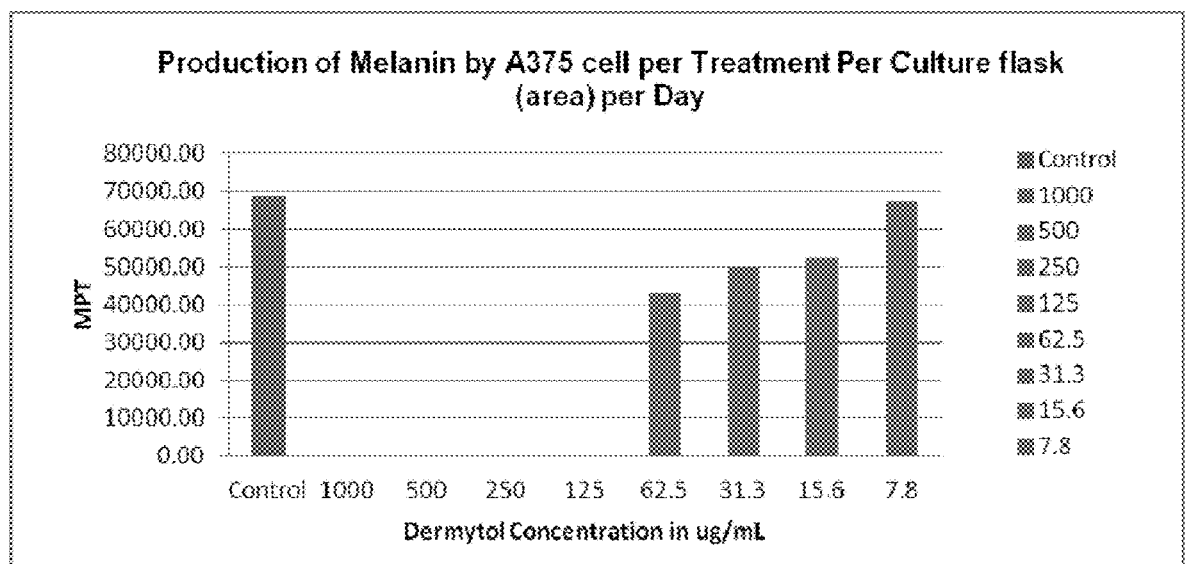
FIG. 5 is a bar chart illustrating the effects of a high phenolic acid canola extract on production of melanin by A375 Cells after 6 days of culture.

FIG. 5 illustrates the effect of Dermytol™ on production of melanin by A375 Cells After 6 days of Culture (MPT).

Biological and cosmetic effects of melanin in vivo are determined by melanin content per area, not per cell. For this reason melanin content per area (culture) is a better parameter than melanin content per cell, for the evaluation of changes in melanin content after treatment in vitro (Dan-Ning, et al). FIG. 5 shows that production of melanin per culture flask per day was inversely proportionate to Dermytol™ treatment doses compared to media control.

Table 6 below represents percent Inhibition per treatment per flask per day.

TABLE 6

| Treatment Conc. ug/mL | % Inhibition of Melanin Production per culture per day |
| --- | --- |
| Control | 0 |
| 1000 | 0 |
| 500 | 0 |
| 250 | 0 |
| 125 | 0 |
| 62.5 | 37.54 |
| 31.3 | 26.80 |
| 15.6 | 24.07 |
| 7.8 | 2.24 |

Figure 6:
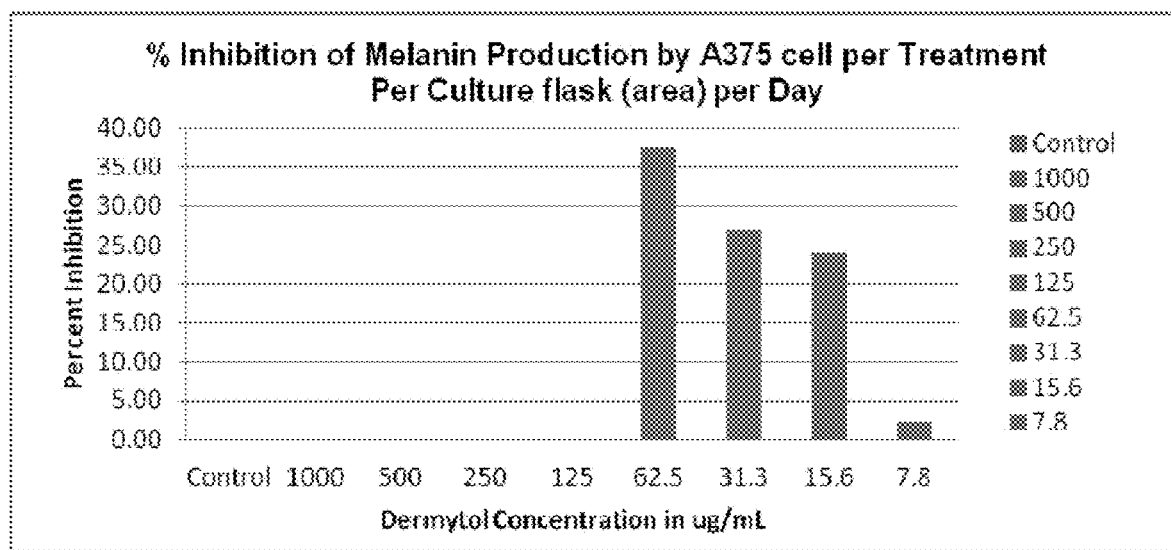
FIG. 6 is a bar chart illustrating the effects of a high phenolic acid canola extract on inhibition of melanin production by A375 Cells after 6 days of treatment.

FIG. 6 further illustrates the effect of Dermytol™ on inhibition of melanin production by A375 Cells after 6 days of treatment. This graph shows that at concentration 62.5 ug/mL the melanin production by A375 cells was decreased by 37.54% compare to the controls. A dose dependent inhibition response can also be seen in FIG. 6.

We claim:

1. A non-therapeutic method for lightening skin comprising the steps of:
   identifying skin where lightening or whitening is desired; and
   topically applying a topical formulation to the skin, the topical formulation comprising:
   (a) a skin lightening agent comprising a canola extract, and
   (b) a cosmetically acceptable carrier,
   wherein the canola extract comprises protocatechuic acid, vanilic acid, caffeic acid, syringic acid, P-coumaric acid, and sinapic acid, and
   wherein the canola extract provides from 0.1% to 5% sinapic acid by weight of the formulation; and
   wherein the canola extract comprises a dose of phenolic acids present in a concentration between about 0.1 µg/ml and about 1000 µg/ml.

2. The method of claim 1, wherein the canola extract further comprises a compound selected from the group consisting of a carotenoid, a tocopherol/sterol, a glucosinolate, and any combination thereof.

3. The method of claim 2, wherein the canola extract comprises a glucosinolate selected from the group consisting of progoitrin, sinigrin, glucoraphanin, napoleferin, glucoalyssin, gluconapin, 4-hydroxybrassicin, glucobrassicanapin, glucobrassicin, gluconasturtin, 4-methoxy-glucobrassicin, neoglucobrassicin, and any combination thereof.

4. A non-therapeutic method for treating hyperpigmentation comprising the steps of:
   identifying skin containing areas of hyperpigmentation; and
   topically applying a topical formulation to the skin, the topical formulation comprising:
   (a) a canola extract, and
   (b) a cosmetically acceptable carrier,
   wherein the canola extract comprises protocatechuic acid, vanilic acid, caffeic acid, syringic acid, P-coumaric acid, and sinapic acid, and wherein the canola provides from 0.1% to 5% sinapic acid by weight of the formulation; and
   wherein the canola extract comprises a dose of phenolic acids present in a concentration between about 0.1 µg/ml and about 1000 µg/ml.

5. The method of claim 4, wherein the canola extract further comprises a compound selected from the group consisting of a carotenoid, a tocopherol/sterol, a glucosinolate, and any combination thereof.

6. The method of claim 5, wherein the canola extract comprises a glucosinolate selected from the group consisting of progoitrin, sinigrin, glucoraphanin, napoleferin, glucoalyssin, gluconapin, 4-hydroxybrassicin, glucobrassicanapin, glucobrassicin, gluconasturtin, 4-methoxy-glucobrassicin, neoglucobrassicin, and any combination thereof.

7. The method of claim 1, wherein the sinapic acid is in an amount of 0.236625% (w/w) in the canola extract.

8. The method of claim 1, wherein the total of phenolic acids of protocatechuic acid, vanilic acid, caffeic acid, syringic acid, P-coumaric acid, and sinapic acid in the canola extract is 0.368902% (w/w).

9. The method of claim 1, wherein the protocatechuic acid is in an amount of 0.019233% (w/w) in the canola extract.

10. The method of claim 1, wherein the vanilic acid is in an amount of 0.009704% (w/w) in the canola extract.

11. The method of claim 1, wherein the caffeic acid is in an amount of 0.0439% (w/w) in the canola extract.

12. The method of claim 1, wherein the syringic acid is in an amount of 0.014985% (w/w) in the canola extract.

13. The method of claim 1, wherein the P-coumaric acid is in an amount of 0.044455% (w/w) in the canola extract.

14. The method of claim 2, wherein the canola extract further comprises a dose of tocopherol/sterol present in a concentration of between about 0.1 µg/ml and about 500 µg/ml.

15. The method of claim 2, wherein the canola extract comprises a glucosinolate, and
   wherein the canola extract comprises a dose of glucosinolates present in a concentration of between about 0.1 µg/ml to about 1000 µg/ml.

* * * * *